United States Patent [19]

Maruyama et al.

[11] Patent Number: 4,660,572
[45] Date of Patent: Apr. 28, 1987

[54] CONTAINER, FOR FIXING AN ANIMAL TO BE TESTED IN A BIOCHEMICAL TEST

[75] Inventors: Yuji Maruyama, 1565-59, Notsuke-machi, Takasaki-shi, Gumma-ken; Kohei Otake, Kawagoe; Hisao Kizaki, Kamifukuoka, all of Japan

[73] Assignees: Yuji Maruyama, Notsuke; New Japan Radio Co., Ltd., Tokyo, both of Japan

[21] Appl. No.: 712,502

[22] Filed: Mar. 18, 1985

[30] Foreign Application Priority Data

Mar. 22, 1984 [JP] Japan ................. 59-55078

[51] Int. Cl.$^4$ ............................................. A61N 5/02
[52] U.S. Cl. ............................ 128/804; 219/10.55 F
[58] Field of Search ............................ 128/804, 399; 219/10.55 R, 10.55 A, 10.55 F

[56] References Cited

U.S. PATENT DOCUMENTS 2,407,690  9/1946  Southworth ................. 128/804 X
3,077,195  2/1963  Folsche ........................ 128/804
4,378,806  4/1983  Henley-Cohn ................ 128/804

FOREIGN PATENT DOCUMENTS 0073709  3/1983  European Pat. Off. ............ 128/804
2122092  1/1984  United Kingdom ................ 128/804

OTHER PUBLICATIONS

Moroji et al., "Rapid Microwave . . . Brain", J. Microwave Power, 12(4), Dec. 1977, pp. 273-286.
"A Microwave Applictaor for In Vivo Rapid Inactivation of Enzymes in the Central Nervous System", IEE Transactions on Microwave Theory and Techniques, MTT-24, No. 1, pp. 58-61 (Jan. 1976).

Primary Examiner—Lee S. Cohen
Attorney, Agent, or Firm—Armstrong, Nikaido, Marmelstein & Kubovcik

[57] ABSTRACT

A container for fixing an animal to be tested in a biochemical test comprises a tubular portion for covering a head of the animal, and a body portion for covering a body of the animal, wherein a microwave is applied to the tubular portion projected into an applicator, the container being improved in that at least a part of the tubular portion is made of a material having a high dielectric constant and a high dielectric loss. The container can make the interior of the head of the animal to be uniformly heated.

5 Claims, 16 Drawing Figures

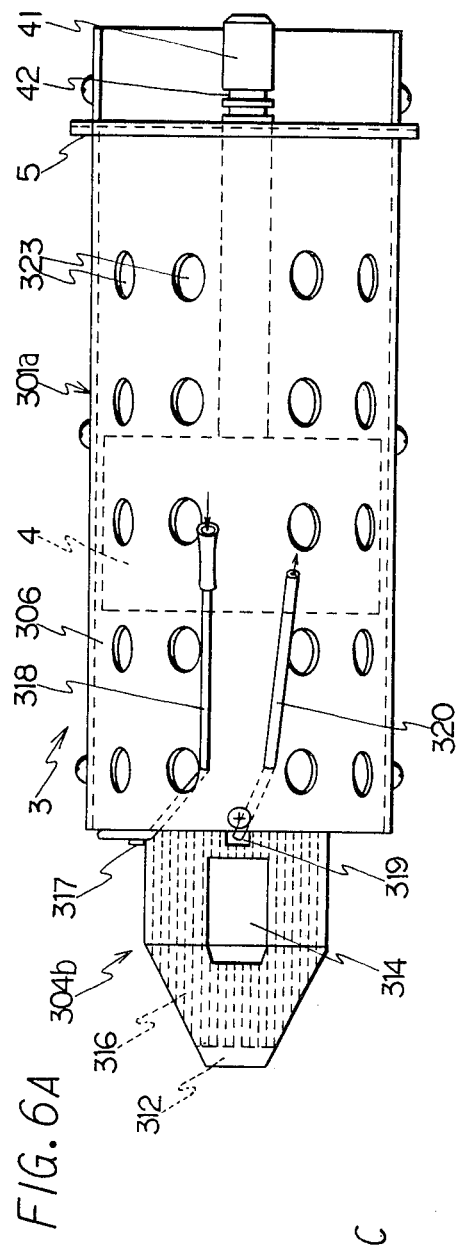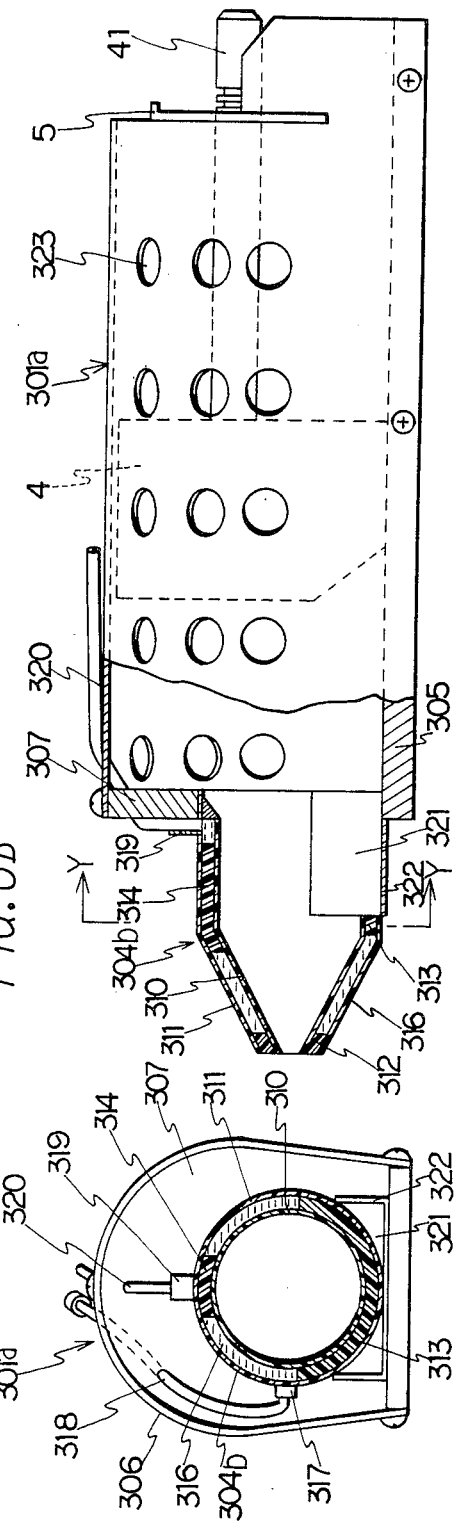

CONTAINER, FOR FIXING AN ANIMAL TO BE TESTED IN A BIOCHEMICAL TEST

BACKGROUND OF THE INVENTION

The present invention relates to a container for fixing an animal to be tested in a biochemical test of pharmacological or biochemical field. Such a container is used when enzymes existing in cells of a brain of the animal are deactivated in a moment with a microwave for the purpose of researching a distribution of the enzymes.

Hitherto, there are known two methods for heating with a microwave, one of which is a method where a microwave is applied to an object to be heated within an oven such as an electronic oven, and the other is a method where an object to be heated is put in a microwave transmission line such as a waveguide in which a microwave is transmitted. The latter method is effective to heat the object in a moment. However, the more a ratio of a sectional area of the object to be heated to a sectional area of the waveguide is increased, the larger becomes the temperature difference in the interior of the object, since the object to be heated is affected by a distribution of an electric field.

FIG. 1 is a sectional view showing a conventional microwave-heating-apparatus which employs the microwave transmission line. In FIG. 1, a waveguide, which is operated in $TE_{10}$ mode and which generates an electric field in the direction of Arrow E, is used as a transmission line. An applicator 1 is formed by short-circuiting a finished end of the waveguide having a terminating plate 11 to short-circuit. An opening 13 is provided on a wall 12 of the applicator 1. The position of the opening is apart from the short-circuiting plate 11 by a predetermined distance. A head 21 of an animal 2 such as mouse or rat is inserted into the applicator 1 through the opening 13.

That is to say, the animal 2 is pushed into the container 3 by a pushing member 4 in a state that the head 21 is directed forward. The motion of the animal 2 is stopped by fixing the pushing member 4. The pushing member 4 is fixed by engaging an engaging plate 5 with a cutting portion 303 of the container 3. Numeral 41 indicates a shaft of the pushing member 4. Numeral 42 indicates grooves provided on the pushing member 4. The goove 42 is engaged with the engaging plate 5.

A tubular chamber 6 is secured to the applicator 1 so that an end of the tubular chamber 6 surrounds the opening 13 of the applicator 1 and the tubular chamber 6 extends from the opening 13 outwardly in an axial direction of the opening 13. The container 3 has a body portion 301 for covering a body of the animal, and a tubular portion 302 for covering a head 21 of the animal 2. The container 3 is inserted into the tubular chamber 6. In that case, the tubular portion 302 of the container 3 projects into the interior of the applicator 1 through the opening 13. The tubular portion 302 is made of a material having a high transparency, a low dielectric constant and a low dielectric loss such as a plastic.

However, in such a microwave-heating-apparatus, when the microwave of $TE_{10}$ mode travels within the applicator 1 in the direction of Arrow A, an electric field E within the applicator 1 has a maximum value at a point on a central axial line a of the waveguide and an electric power ($aE^2$) within the applicator 1 has an excessive maximum value at the point on the central axial line a of the waveguide (shown in FIG. 2A).

Accordingly, when the head 21 to be heated of the animal 2 is very small in volume and size in comparison with a wavelength-in-waveguide $\lambda_g$ of the used microwave, the temperature difference in the interior of the head 21 is so small that the difference can be ignored. However, in proportion to the increase in volume and size of the head 21 to be heated, the temperature difference in the interior of the head 21 becomes so large that the difference cannot be ignored, due to the excessive affection of a distribution of an electric field.

Particularly, when the microwave is applied to the head 21 until both sides of the head 21 are sufficiently heated, a part of the head 2a on the central axial line a is excessively heated. As a result, an important and fine brain tissue, such as a hypothalamus, existing on the central axial line a is easily destroyed.

When the head 21 of the tested animal 2 rotates a little in the direction of Arrow B shown in FIG. 2B under heating, the temperature difference between a right side and a left side of the head 21 is increased. That is to say, one side of the brain 22 is excessively heated and the other side of the brain 22 is insufficiently heated. In that case, it is impossible to uniformly heat the brain 22. As a result, a distribution of enzymes in the brain cannot be disadvantageously researched.

OBJECT OF THE INVENTION

The object of the present invention is to provide a container for fixing an animal to be tested in a biochemical test, capable of making the interior of the head of the animal to be uniformly heated.

SUMMARY OF THE INVENTION

In accordance with the present invention, there is provided a container for fixing an animal to be tested in a biochemical test comprising a tubular portion for covering a head of the animal, and a body portion for covering a body of the animal, wherein a microwave is applied to the tubular portion projected into an applicator, the container being improved in that at least a part of the tubular portion is made of a material having a high dielectric constant and a high dielectric loss.

The above and other objects and the advantages of the present invention will become apparent from the following description with the accompanying drawings.

BRIEF DESCRIPTION OF THE DRAWINGS

FIG. 6A is a plan view showing other embodiment of the container of the present invention;

FIG. 6B is a side view of the container in FIG. 6A, in which a tubular portion of the container is sectionally illustrated;

FIG. 6C is a sectional view taken along line Y—Y of FIG. 6B;

FIG. 7B is a partial sectional view of the tubular portion in FIG. 7a.

DETAILED DESCRIPTION OF THE INVENTION

Figure 3A:
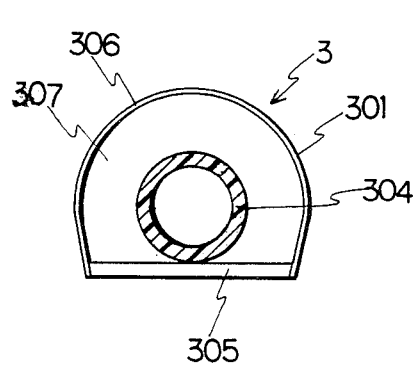
FIG. 3A is a front view showing an embodiment of a container for fixing an animal to be tested of the present invention.
Figure 3B:
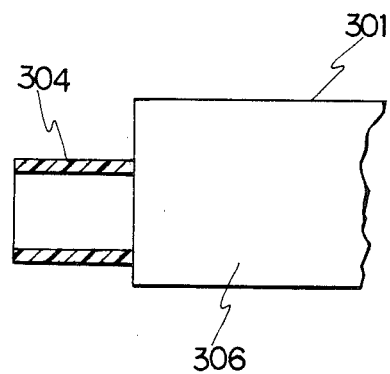
FIG. 3B is a partial side view of the container in FIG. 3A, in which a tubular portion of the container is sectionally illustrated.

In FIGS. 3A and 3B, a container 3 for fixing an animal to be tested has a body portion 301. The body portion 301 comprises a base plate 305 and a U-shaped plate 306. A connecting plate 307 connects a tubular portion 304 with the body portion 301. The tubular portion 304 is made of a material having a high dielectric constant and a high dielectric loss (hereinafter referred to as "dielectric material"), such as ferrite or ceramic (regulated in values of $\epsilon_s$ and tan $\delta$) having $\epsilon_s = 50$, tan $\delta = 0.26$.

When the microwave is applied to the tubular portion 304 made of the dielectric material, the tubular portion 304 absorbs the microwave in itself. As a result, there can be obtained an effect similar to the effect that the head 21 of the animal 2 located within the tubular portion 304 is increased in volume. Consequently, the curve of the temperature distribution within a brain 22 can be made into a curve having a gradual slope.

Figure 5A:
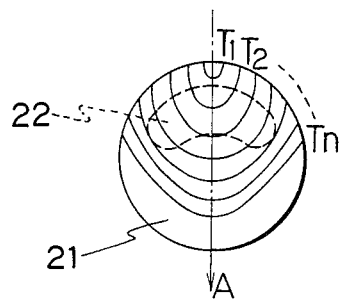
FIG. 5A is a diagram of a temperature distribution within the head of the animal when the conventional container is employed.
Figure 5B:
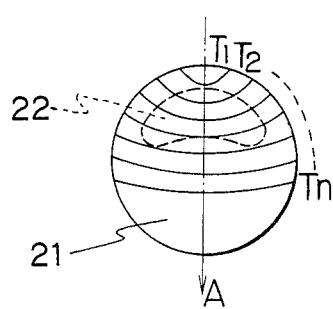
FIG. 5B is a diagram of a temperature distribution within the head of the tested animal when the container in FIG. 3A is employed.
Figure 5C:
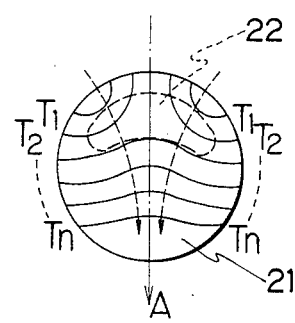
FIG. 5C is a diagram of a temperature distribution within the head of the animal when the container in FIG. 4A is employed.

That is to say, as shown in FIG. 5B, a temperature difference between a central portion and a side portion of the head 21 is decreased so that the interior of the head 21 is approximately uniformly heated. In FIGS. 5A to 5C, temperatures $T_1, T_2, \ldots, T_n$ are related with each other as follows:

$$T_1 > T_2 > \ldots > T_n$$

When a conventional tubular portion made of a material having a low dielectric constant and a low dielectric loss is employed, the temperature difference between the central portion and the side portion of the brain is large as shown in FIG. 5A. That is to say, the temperature of the brain on the central axial line of electric field of the microwave is the highest, and the temperature falls toward the side portion.

Figure 1:
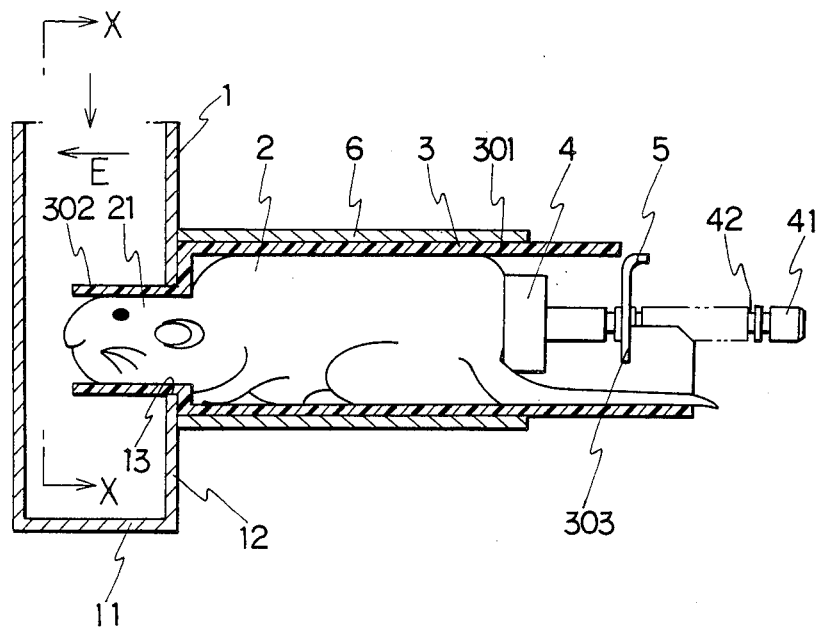
FIG. 1 is a sectional view showing a microwave-heating-apparatus employing a conventional container for fixing an animal to be tested.
Figure 2A:
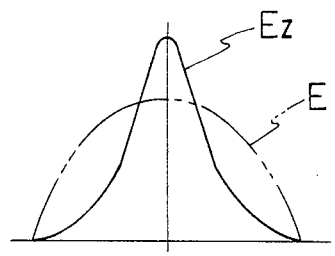
FIG. 2A is a diagram showing each distribution of an electric field and an electric power within an applicator of the microwave-heating-apparatus in FIG. 1.
Figure 2B:
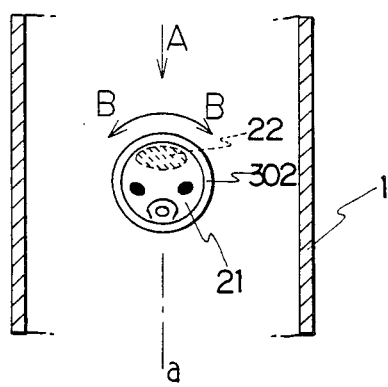
FIG. 2B is a sectional view taken along line X—X of FIG. 1.

In such an embodiment of the container of the present invention, when the microwave is applied in the direction of Arrow A (shown in FIG. 1), the microwave is attracted toward the tubular portion 304, since the tubular portion 304 is made of the above dielectric material. The extent that the tubular portion 304 attracts the microwave is dependent on a value of $\epsilon \cdot \tan \delta$ of the tubular portion 304, diameter, thickness and length of the tubular portion 304, and size of the head 21 of the animal 2, and $\epsilon \cdot \tan \delta$ of the head 21 of the animal 2, and the like. An optimum value of each factor is obtained by experiment. Particularly, when the value of $\epsilon \cdot \tan \delta$ of the tubular portion 304 is large, excessive destruction of the brain 22 can be reduced, since a microwave-absorbance in the tubular portion is increased, that is to say, the microwave transmitted into the brain 22 is decreased.

Figure 4A:
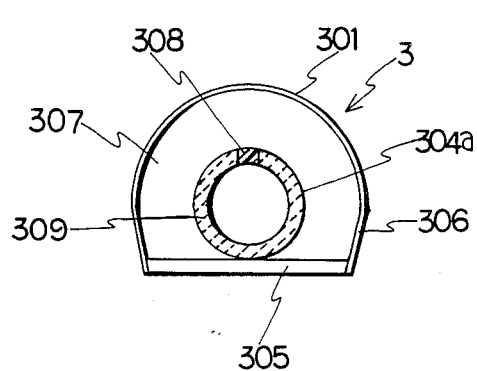
FIG. 4A is a front view showing another embodiment of the container of the present invention.
Figure 4B:
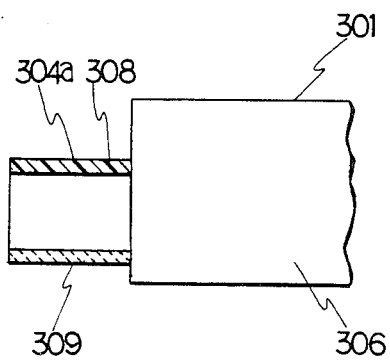
FIG. 4B is a partial side view of the container in FIG. 4A, in which a tubular portion of the container is sectionally illustrated.
Figure 4C:
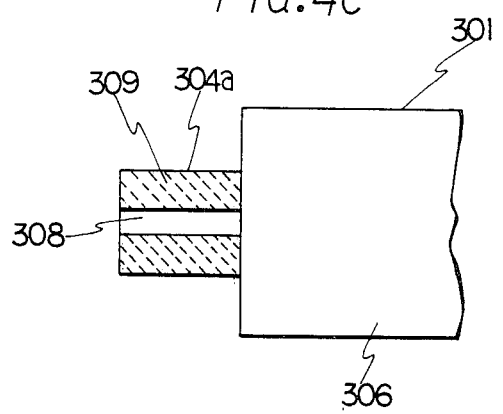
FIG. 4C is a partial plan view of the container in FIG. 4A.

FIGS. 4A to 4C show another embodiment of the container of the present invention. In the container, the tubular portion 304a of the container 3 comprises a first part 308 facing to a microwave front to which the microwave approaches, and a remained part 309. The first part 308 is made of a material having a low dielectric constant and a low dielectric loss, such as a polycarbonate having $\epsilon_s = 2.5$, tan $\delta = 0.01$. The remained part 309 is made of the above dielectric material having $\epsilon_s = 50$, tan $\delta = 0.26$.

According to such a structure, when the tubular portion 304a is located at a central portion within the applicator and the first part 308 of the tubular portion 304a is faced to the microwave front to which the microwave approaches, the brain 22 of the head 21 within the tubular portion 304a is prevented from excessively heating.

In that case, the microwave is prevented to some extent from passing through the first part 308, that is to say, the microwave which turns toward each side of the tubular portion 304a increases. Therefore, a distribution of temperature, which would be obtained when two microwaves are applied to the tubular portion 304a, can be obtained. As a result, the temperature is uniformly distributed in the plane perpendicular to the direction that the microwave is transmitted, and the head 2a of the animal 2 is approximately uniformly heated. Further, even if the head 21 rotates within the tubular portion 304a, the head 21 is approximately uniformly heated.

Though the first part 308 is made of a polycarbonate, or the like, it is not necessary to provide such a first part 308. That is to say, a cutting part in which air exists is provided at the position corresponding to the above first part 308 of the tubular portion 304a. In that case, since the air existing in the cutting part has a low dielectric constant and a low dielectric loss, an effect similar to the effect of the above first part 308 made of the polycarbonate, or the like, can be obtained. Therefore, the work for forming the first part made of the polycarbonate, or the like, can be removed.

FIGS. 6A to 6C show another embodiment of the container of the present invention. In FIGS. 6A to 6C, a tubular portion 304b of the container comprises an inner tubular part 310 and an outer tubular part 311. A material having a high dielectric constant and a high dielectric loss is provided in a space between the inner tubular part 310 and the outer tubular part 311.

In detail, the tubular portion 304b is tapered toward a free end. A plug 312 made of a material having a low dielectric constant and a low dielectric loss is provided on the free end. Near the other end of the tubular portion 304b opposite to the free end, a lower portion between the inner tubular part 310 and the outer tubular part 311 is closed by a material 313 having a low dielectric constant and a low dielectric loss, and its upper portion is closed by a material 314 having a low dielectric constant and a low dielectric loss, such as a plastic material, or the like. A remained space between the inner tubular part 310 and the outer tubular part 311 is filled with a liquid-dielectric-material 316 such as water or a solution of salt.

Numeral 317 indicates an inlet portion for feeding the liquid-dielectric-material 316 into the remained space. The inlet portion 317 is connected with an inlet pipe 318. Numeral 319 indicates an outlet portion for discharging the liquid-dielectric-material 316 out of the remained space. The outlet portion 319 is connected with an outlet pipe 320. Numeral 321 indicates a space for projecting forelegs of an animal. Numeral 322 indicates a stage on which the forelegs of the animal are put. The end of the tubular portion 304b at the side of the body portion 301a is closed by another plug (not shown).

In such an embodiment, a function of the material 314 having a low dielectric constant and a low dielectric loss is similar to the function of the above first part 308.

In the embodiment in FIGS. 6A to 6C, a base plate 305 and a U-shape plate 306 of the body portion 301a are made of a metal so that the interior of the body portion 301a can be darkened. The U-shape plate 306 has a plurality of opening 323 for introducing light a little. A connecting plate 307 made of a material having a low dielectric constant and a low dielectric loss connects the tubular portion 304b with the body portion 301a.

In such a container for fixing an animal, it is possible that the animal per se having the nocturnal habits, such as mouse or rat comes into the container, since the interior of the container is darkened. Therefore, it is not necessary to push the animal into the container, and the animal can be prevented from being stressed, so that good experimental data can be repeatedly obtained.

When the thicknesses of the inner tubular part 310 and the outer tubular part 311 are made thin enough to maintain the mechanical strength, the inner tubular part and the outer tubular part can be made of materials having a high dielectric constant and a high dielectric loss.

Figure 7A:
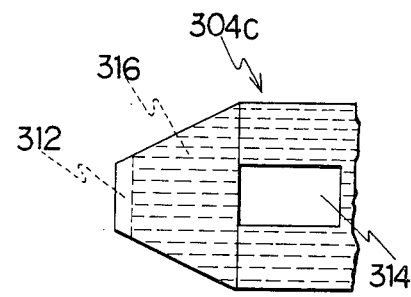
FIG. 7A is a partial plan view of a tubular portion of other embodiment of the container of the present invention.
Figure 7B:
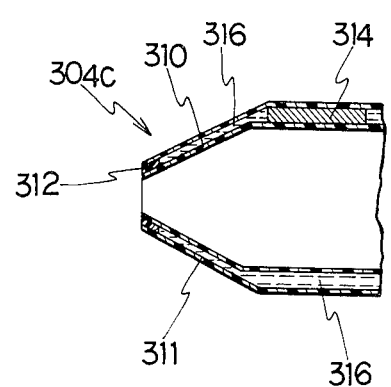

FIGS. 7A and 7B show another embodiment of the container for fixing an animal. The tubular portion 304c is not provided with the space 321 and the stage 322 in FIGS. 6A to 6C. Further, though the tubular portion 304C has an inner tubular part 310 and an outer tubular part 311 similar to the embodiment in FIGS. 6A to 6C, the gap (between the inner tubular part and the outer tubular part) at the tapered side of the tubular portion 304c is different from the gap at the opposite side of the tubular portion 304c. Therefore, a thickness of a remained space between the inner tubular part and the outer tubular part is changed so that the thickness of the above liquid dielectric material 316 within the remained space can be changed.

In such an embodiment, the amount of absorption of the microwave can be changed along an axial line of the tubular portion 304c.

In the embodiments in FIGS. 3A, 3B, 4A, 4B and 4C, the tubular parts 304, 304a may be formed by an inner tubular part and an outer tubular part and may define the above liquid dielectrical material in a space between the inner tubular part and the outer tubular part.

In the above described embodiments, as to the material having a high dielectric constant and a high dielectric loss, the values of $\epsilon_s$ and tan $\delta$ are respectively determined as $\epsilon_s = 20$ to $140$ and tan $\delta = 0.1$ to $1.0$. Examples of the dielectric material are, for instance, ferrite, ceramic (regulated in values of $\epsilon_s$ and tan $\delta$), and the like. When such a material is employed, a good result can be obtained.

According to the present invention, a good experimental data can be obtained, since the heating distribution within the tubular portion in which the head of the animal is inserted, substantially becomes uniform.

What we claim is:

1. In a container for fixing an animal to be tested in a biochemical test comprising a hollow tubular portion for covering a head of the animal, and connected thereto at one end thereof a hollow body portion for covering a body of the animal, wherein a microwave is applied to said tubular portion projected into an applicator, the improvement wherein the tubular portion is made of a material having a high dielectric constant and a high dielectric loss, and a part of the tubular portion facing to a microwave to where the microwave approaches is partially removed or replaced by a material having a low dielectric constant and a low dielectric loss.

2. The container of claim 1, where said tubular portion is constituted of double walls, and a portion of space between the double walls is filled with a material having a high dielectric constant and a high dielectric loss.

3. The container of claim 2, wherein the material in said space between said double walls is a liquid.

4. The container of claim 3, wherein the liquid is water.

5. The container of claim 3, wherein the liquid is a solution of salt.

* * * * *